United States Patent
Sugimoto et al.

(10) Patent No.: US 9,733,200 B2
(45) Date of Patent: Aug. 15, 2017

(54) DEFECT JUDGING DEVICE, RADIOGRAPHY SYSTEM, AND DEFECT JUDGING METHOD

(71) Applicant: MITSUBISHI HEAVY INDUSTRIES, LTD., Tokyo (JP)

(72) Inventors: Kiichi Sugimoto, Tokyo (JP); Yosuke Fujitomi, Tokyo (JP); Tsuyoshi Tomita, Tokyo (JP); Atsushi Kiya, Tokyo (JP); Akemi Takano, Tokyo (JP); Hidenori Takeda, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/402,534

(22) PCT Filed: Jun. 7, 2013

(86) PCT No.: PCT/JP2013/065822
§ 371 (c)(1),
(2) Date: Nov. 20, 2014

(87) PCT Pub. No.: WO2013/183758
PCT Pub. Date: Dec. 12, 2013

(65) Prior Publication Data
US 2015/0131779 A1     May 14, 2015

(30) Foreign Application Priority Data

Jun. 8, 2012  (JP) .................................. 2012-130713

(51) Int. Cl.
*G06K 9/00*     (2006.01)
*G01N 23/18*    (2006.01)
*G01N 23/04*    (2006.01)

(52) U.S. Cl.
CPC ............. *G01N 23/18* (2013.01); *G01N 23/04* (2013.01)

(58) Field of Classification Search
None
See application file for complete search history.

(56) References Cited

U.S. PATENT DOCUMENTS

| 8,135,204 B1 * | 3/2012 | Chen .................. G01N 21/9501 250/310 |
| 2006/0067570 A1 * | 3/2006 | Onishi .................... G06T 7/001 382/147 |

(Continued)

FOREIGN PATENT DOCUMENTS

| CN | 101251496 | 8/2008 |
| JP | 60-250236 | 12/1985 |

(Continued)

OTHER PUBLICATIONS

International Search Report issued Aug. 20, 2013 in International Application No. PCT/JP2013/065822.

(Continued)

*Primary Examiner* — Sumati Lefkowitz
*Assistant Examiner* — David Perlman
(74) *Attorney, Agent, or Firm* — Wenderoth, Lind & Ponack, L.L.P.

(57) ABSTRACT

With an image processing device, a presence/absence of a product defect is judged based on detected-image data obtained by a radiographic device that detects radiation that has passed through a product, which is an inspection subject. With the image processing device, a position of a product feature in the detected-image data is identified based on a shape of the product feature indicated by feature data stored in a storage portion in advance, defect candidates are extracted with reference to the identified product feature in the detected-image data, and the presence/absence of a (Continued)

product defect is judged based on characteristic quantities of product defects indicated by a defect characteristic stored in the storage portion in advance and characteristic quantities of the defect candidates.

9 Claims, 7 Drawing Sheets

(56) References Cited

U.S. PATENT DOCUMENTS

| | | | | |
|---|---|---|---|---|
| 2007/0156379 | A1* | 7/2007 | Kulkarni | H01L 21/67005 703/14 |
| 2007/0202476 | A1 | 8/2007 | Williamson | |
| 2009/0097729 | A1 | 4/2009 | Venkatachalam et al. | |
| 2009/0136121 | A1 | 5/2009 | Nakagaki et al. | |
| 2009/0154829 | A1 | 6/2009 | Jung et al. | |
| 2010/0074516 | A1* | 3/2010 | Kawaragi | G01N 21/956 382/149 |
| 2010/0119144 | A1* | 5/2010 | Kulkarni | H01L 21/67005 382/149 |
| 2011/0113825 | A1* | 5/2011 | Neeraas | F25J 1/0022 62/613 |
| 2012/0069173 | A1 | 3/2012 | Takahashi et al. | |

FOREIGN PATENT DOCUMENTS

| | | |
|---|---|---|
| JP | 3-209583 | 9/1991 |
| JP | 7-16151 | 3/1995 |
| JP | 8-96136 | 4/1996 |
| JP | 2000-76446 | 3/2000 |
| JP | 2001-77165 | 3/2001 |
| JP | 2002-56476 | 2/2002 |
| JP | 2002-236759 | 8/2002 |
| JP | 2003-530546 | 10/2003 |
| JP | 2005-117513 | 4/2005 |
| JP | 2007-127601 | 5/2007 |
| JP | 2008-96425 | 4/2008 |
| JP | 2008-292405 | 12/2008 |
| JP | 2009-516832 | 4/2009 |
| JP | 2009-123851 | 6/2009 |
| JP | 2009-153942 | 7/2009 |
| KR | 10-2009-0018920 | 2/2009 |

OTHER PUBLICATIONS

Written Opinion of the International Searching Authority issued Aug. 20, 2013 in International Application No. PCT/JP2013/065822.

Noriyuki Sadaoka, Tatsuro Yashiki, "Sangyo-yo X-sen CT ni yoru Digital Engineering to Turbine kiki eno katsuyo", Gas Turbine Seminar Shiryoshu, vol. 35th, pp. 97-103, ISSN 1341-8491, Jan. 19, 2007.

First Office Action issued Jan. 6, 2016 in corresponding Chinese Application No. 201380023962.2 (with English translation).

Notice of Allowance issued Jul. 27, 2016 in corresponding Korean Application No. 10-2014-7031282 (with English translation).

The Notice of Preliminary Rejection issued Apr. 1, 2016 in corresponding Korean Patent Application No. 10-2014-7031282 (with English translation).

Decision of Patent Grant issued Apr. 26, 2016 in corresponding Japanese Patent Application No. 2012-130713 (with English translation).

* cited by examiner

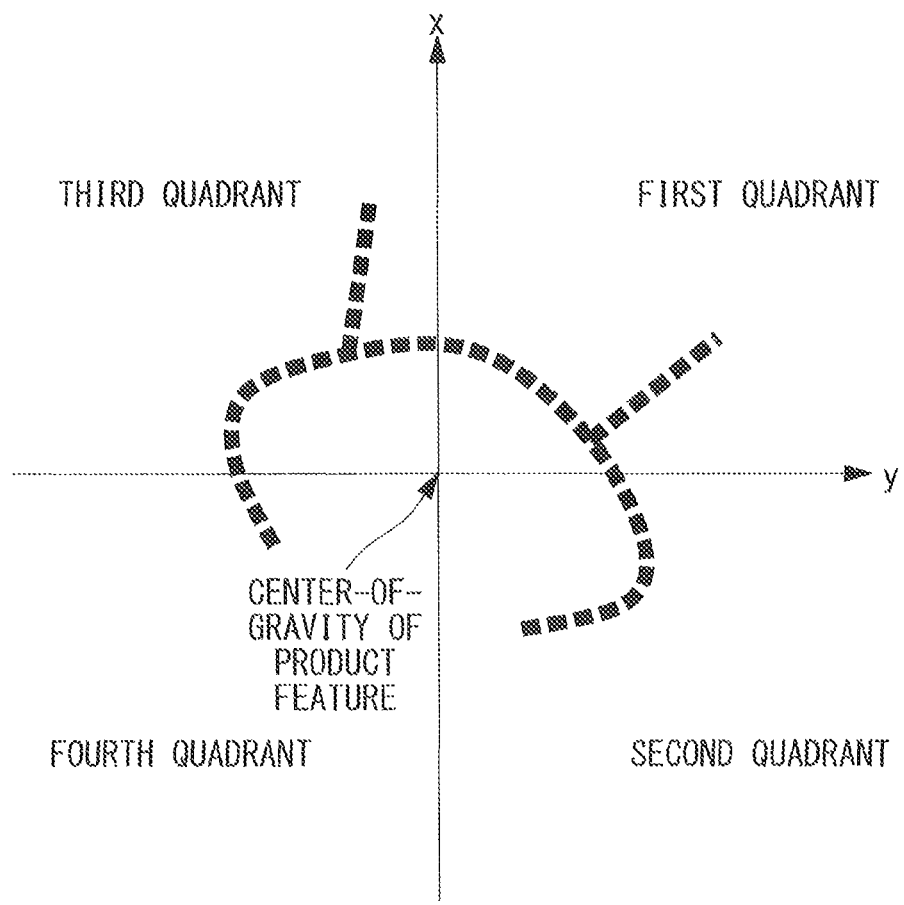

DEFECT JUDGING DEVICE, RADIOGRAPHY SYSTEM, AND DEFECT JUDGING METHOD

TECHNICAL FIELD

The present invention relates to a defect judging device, a radiography system, and a defect judging method.

BACKGROUND ART

A radiographic device radiates radiation (for example, X-rays) onto an inspection subject and obtains detected-image data by detecting the radiation that has passed through the inspection subject. These detected-image data are obtained by, for example, detecting the radiation by means of an FPD (Flat panel detector).

Although an FPD is formed of a plurality of detection elements, among the detection elements, those having an abnormality in outputting detection signals in response to the irradiated radiation sometimes appear in the form of a line.

Japanese Unexamined Patent Application, Publication No. 2009-153942 discloses a radiographic device that applies edge emphasizing processing to a captured image, that makes a judgment on line-abnormality imaging elements by setting a predetermined threshold, that makes the line-abnormality imaging elements conspicuous by further emphasizing them, and that generates detected-image data showing the difference after applying the edge emphasizing processing, thus making it possible to more precisely detect line-abnormality imaging elements that only have minute changes.

Technical Problem

However, even if the line-abnormality imaging elements are precisely detected, as described in Japanese Unexamined Patent Application, Publication No. 2009-153942, a defect occurring in the inspection subject may not be judged correctly in the case in which the orientation, size, or the like of the inspection subject differs between an initial image that serves as a reference for the presence/absence of a defect occurring in an inspection subject and an image obtained by detecting radiation that has actually passed through the inspection subject.

Because of this, an operator needs to perform work for securing the inspection subject and the radiographic device at predetermined positions, which increases the amount of time required for capturing an image.

SUMMARY OF INVENTION

The present invention has been conceived in light of the above-described circumstance, and an object thereof is to provide a defect judging device, a radiography system, and a defect judging method with which it is possible to judge a defect occurring in an inspection subject with high precision without performing work to fix the relative positions of the inspection subject and a radiographic device to predetermined positions.

Solution to Problem

In order to solve the above-described problems, a defect judging device, a radiography system, and a defect judging method of the present invention employ the following solutions.

A defect judging device according to a first aspect of the present invention is a defect judging device that judges the presence/absence of a defect in the inspection subject based on detected-image data obtained by a radiographic device that detects radiation that has passed through an inspection subject, the defect judging device including a position identifying portion for identifying a position of a feature site in the detected-image data based on a shape of the feature site of the inspection subject indicated by feature data that are stored in a storage portion in advance; and a defect judging portion for extracting a defect candidate with reference to the feature site in the detected-image data identified by the position identifying portion and for judging the presence/absence of a defect in the inspection subject based on a characteristic quantity of a defect indicated by defect characteristic data stored in the storage portion in advance and a characteristic quantity of the defect candidate.

With this configuration, the defect judging device judges a defect in the inspection subject based on the detected-image data obtained by detecting the radiation that has passed through the inspection subject.

Then, the position of the feature site in the detected-image data is identified by the position identifying portion based on the shape of the feature site of the inspection subject indicated by the feature data stored in the storage portion in advance. The position of the feature site is identified by, for example, applying template matching processing to the feature data and the detected-image data. By doing so, the position of the feature site in the detected-image data is identified regardless of the orientation and size of the inspection subject at the time at which the radiographic device radiates the radiation. The feature site in the inspection subject is preferably a site at which a defect tends to occur in the periphery thereof.

The defect candidates are extracted by the defect judging portion with reference to the identified feature site in the detected-image data, and the presence/absence of a defect in the inspection subject is judged based on the characteristic quantities of the defects that occur in the inspection subject indicated by the defect characteristic data stored in the storage portion in advance and the characteristic quantities of the defect candidates. Because the presence/absence of a defect is judged in this way based on the characteristic quantities of the defects indicated by the defect characteristic data and the characteristic quantities of the defect candidates, defect judgment can be performed with high precision.

Therefore, with this configuration, it is possible to judge a defect occurring in an inspection subject with high precision without performing work to fix the relative positions of the inspection subject and the radiographic device to predetermined positions.

In the above-described first aspect, it is preferable that the defect judging portion determine a position of the defect candidate with respect to the feature site and judge the presence/absence of a defect in the inspection subject based on the characteristic quantity of the defect indicated by the defect characteristic data in accordance with that position and the characteristic quantity of the defect candidate.

With this configuration, it is possible to more precisely judge the presence/absence of a defect based on the position of the defect candidate with respect to the feature site.

In the above-described first aspect, it is preferable that defects whose Euclidean distances are equal to or less than a predetermined threshold be assumed to be a single group and that the defect characteristic data indicate characteristic quantities of the individual groups.

With this configuration, the defects whose Euclidean distances are equal to or less than the predetermined threshold are assumed to be a single group, and because the presence/absence of a defect in the inspection subject is judged based on the characteristic quantities of the groups and the characteristic quantity of the defect candidate, the presence/absence of a defect can be judged in a simpler manner with high precision.

In the above-described first aspect, it is preferable that respective priority ranks be set for the individual groups, and the defect judging portion judge that the defect candidate contained in a presence range of a group having a higher priority rank is more likely to be a defect.

With this configuration, the inspector can easily make the final visual defect judgment for the defect candidates.

In the above-described first aspect, it is preferable that, in the defect characteristic data, defects be classified in accordance with a plurality of regions determined with reference to the position of the feature site, thus showing the characteristic quantity of the defect for the individual regions.

With this configuration, the defect is classified in accordance with a plurality of regions determined with reference to the feature site of the inspection subject, for example, in accordance with the four quadrants whose center is at the center of gravity (centroid) of the feature site. Thus, because the presence/absence of a defect in the inspection subject is judged based on the characteristic quantity of the defect in accordance with the classified regions, the presence/absence of a defect can be judged in a simpler manner with high precision.

In the above-described first aspect, it is preferable that the defect characteristic data be updated by newly incorporating the characteristic quantity of the defect candidate that has been judged to be a defect.

With this configuration, because the characteristic quantities of the defect are accumulated every time the number of times that defect judgment is performed increases, the precision of the defect judgment can be further increased.

A radiography system according to a second aspect of the present invention is a radiography system including a radiographic device that radiates radiation onto an inspection subject and obtains detected-image data by detecting radiation that has passed through the inspection subject and one of the defect judging devices described above.

A defect judging method according to a third aspect of the present invention is a defect judging method that, based on detected-image data obtained by a radiographic device that detects radiation that has passed through an inspection subject, judges the presence/absence of a defect in the inspection subject, the defect judging method including a first step of identifying a position of a feature site in the detected-image data based on a shape of the feature site of the inspection subject indicated by feature data that are stored in a storage portion in advance; and a second step of extracting a defect candidate with reference to the feature site in the detected-image data identified in the first step and of judging the presence/absence of a defect in the inspection subject based on a characteristic quantity of a defect indicated by defect characteristic data stored in the storage portion in advance and a characteristic quantity of the defect candidate.

Advantageous Effects of Invention

The present invention affords an excellent advantage in that it is possible to judge a defect occurring in an inspection subject with high precision without performing work to fix the relative positions of the inspection subject and a radiographic device to predetermined positions.

BRIEF DESCRIPTION OF DRAWINGS

FIG. 8 is a schematic diagram showing an example classification of defect candidates according to a fourth embodiment of the present invention.

DESCRIPTION OF EMBODIMENTS

Embodiments of a defect judging device, a radiography system, and a defect judging method according to the present invention will be described below with reference to the drawings.

First Embodiment

A first embodiment of the present invention will be described below.

Figure 1:
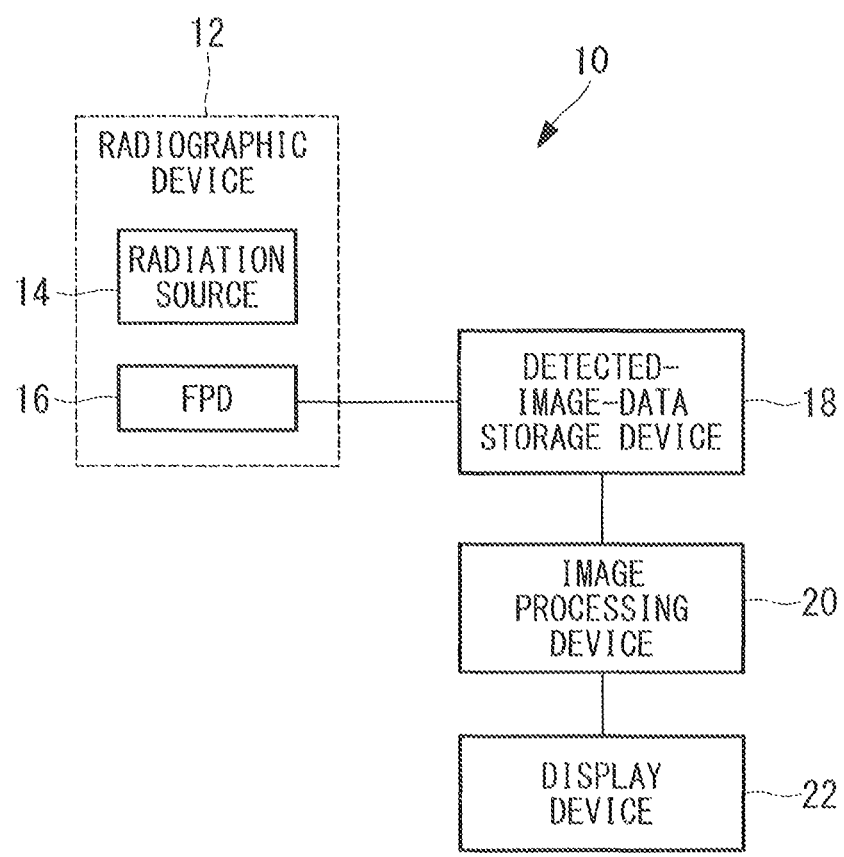
FIG. 1 is a diagram showing the configuration of a radiography system according to a first embodiment of the present invention.

FIG. 1 is a diagram showing the configuration of a radiography system 10.

The radiography system 10 is provided with a radiographic device 12, a detected-image-data storage device 18, an image processing device 20, and a display device 22.

The radiographic device 12 is provided with a radiation source 14 that irradiates an inspection subject (hereinafter referred to as "product") with radiation and an FPD (Flat panel detector) 16 that obtains detected-image data (digital data) by detecting the radiation that has passed through the product. In this first embodiment, the radiation is assumed to be X-rays as an example.

The detected-image-data storage device 18 stores the detected-image data obtained by the FPD 16.

The image processing device 20 reads out the detected-image data stored in the detected-image-data storage device 18 and applies various types of image processing to the detected-image data. This image processing includes defect judging processing for judging the presence/absence of a defect in the product (hereinafter referred to as "product defect") based on the detected-image data. Although the product is assumed to be a gas-turbine blade (a stator blade or a rotor blade) as an example, it is not limited thereto. The detected-image data are assumed to be two-dimensional image data.

The display device 22 displays the results, etc. of the image processing performed by the image processing device 20.

Figure 2:
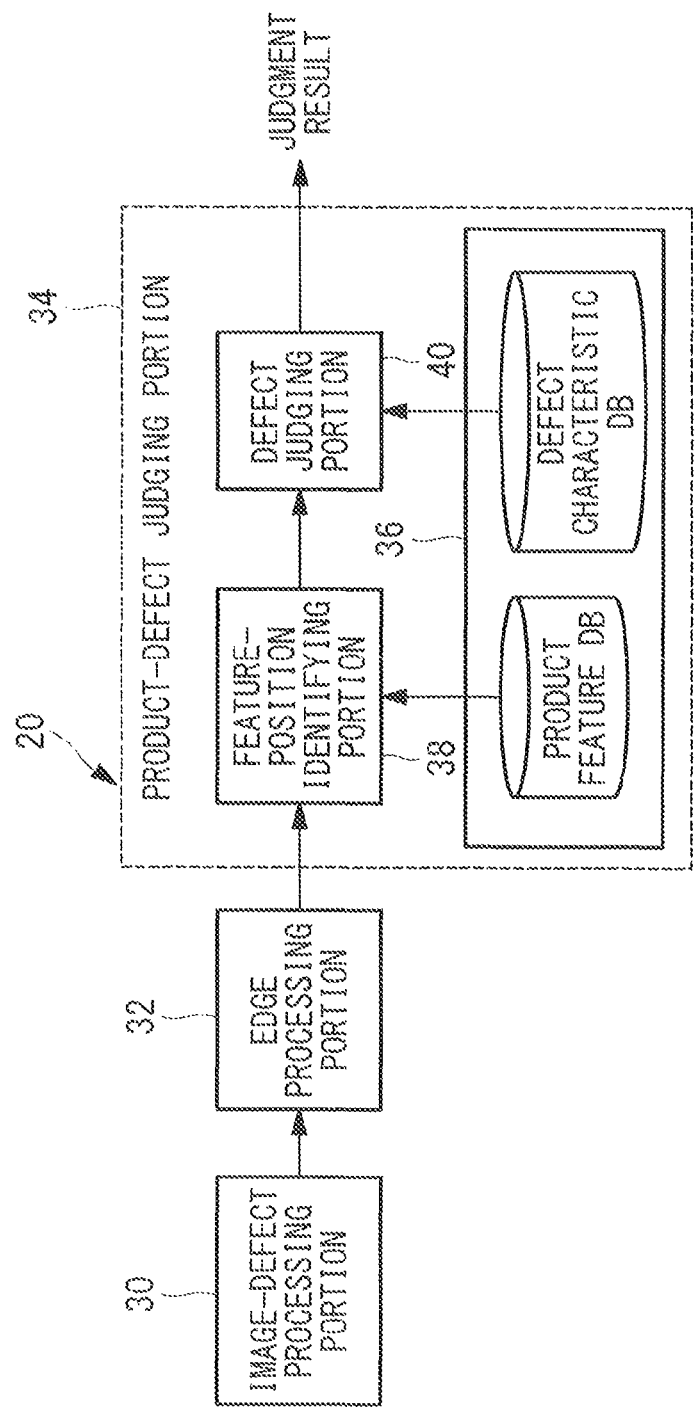
FIG. 2 is a block diagram showing the configuration of an image processing device according to the first embodiment of the present invention.

FIG. 2 is a block diagram showing the configuration of the image processing device 20.

The image processing device 20 is provided with an image-defect processing portion 30, an edge processing portion 32, and a product-defect judging portion 34.

The image-defect processing portion 30 processes defects (hereinafter referred to as "image defect") occurring in the detected-image data. A plurality of detection elements that constitute the FPD 16 sometimes include detection elements that have an abnormality in outputting detection signals in response to the irradiated radiation. Regions in the detected-image data corresponding to these detection elements having an abnormality do not have correct detected-image data. Even if the presence/absence of a product defect is judged based on such detected-image data, a highly precise judgment may not be possible. Therefore, the image-defect processing portion 30 processes the image defects occurring in the detected-image data so as not to affect the judgment of the presence/absence of a product defect.

The edge processing portion 32 makes the outline of an image indicated by the detected-image data clear by applying edge processing to the detected-image data.

The product-defect judging portion 34 is provided with a DB storage portion 36, a feature-position identifying portion 38, and a defect judging portion 40.

The DB storage portion 36 stores in advance a product feature database (hereinafter referred to as "product feature DB") that manages product feature data indicating the shapes of feature sites of the product (hereinafter referred to as "product features") and a defect characteristic database (hereinafter referred to as "defect characteristic DB") that manages defect characteristic data indicating characteristic quantities of the product defects.

It is preferable that the product feature be a site where a product defect tends to occur in the periphery thereof. For example, in the case in which the product is a gas-turbine blade, the product feature is assumed to be a cooling groove provided inside the blade. This groove has a curvature or the like, and a product defect may occur in the surroundings thereof.

Thus, the product defect is, for example, a crack or a spot that occurs in the periphery of the groove.

The feature-position identifying portion 38 performs feature-position identifying processing for identifying the position of the product feature in the detected-image data based on the shapes of the product feature indicated by the product feature data.

The defect judging portion 40 extracts defect candidates with reference to the product feature in the detected-image data identified by the feature-position identifying portion 38 and judges the presence/absence of a product defect (hereinafter referred to as "defect judging processing") based on the characteristic quantities of the product defects (characteristic quantities of a cluster in this first embodiment) indicated by the defect characteristic DB and characteristic quantities of the defect candidates. The results of the judgment performed by the defect judging portion 40 are displayed on the display device 22.

The image processing device 20 is constituted of, for example, a CPU (Central Processing Unit), a RAM (Random Access Memory), a computer-readable recording medium (DB storage portion 36), and so forth. Also, a series of processing for realizing various functions of the image-defect processing portion 30, the edge processing portion 32, the feature-position identifying portion 38, and the defect judging portion 40 are, as an example, stored in a recording medium or the like in the form of programs, and the CPU, the RAM, or the like reads out these programs and executes information manipulation and computational processing, thus realizing the various functions.

Here, the generation of the defect characteristic DB will be described with reference to FIG. 3. The defect characteristic DB is generated in advance as described above and stored in the DB storage portion 36.

Figure 3:
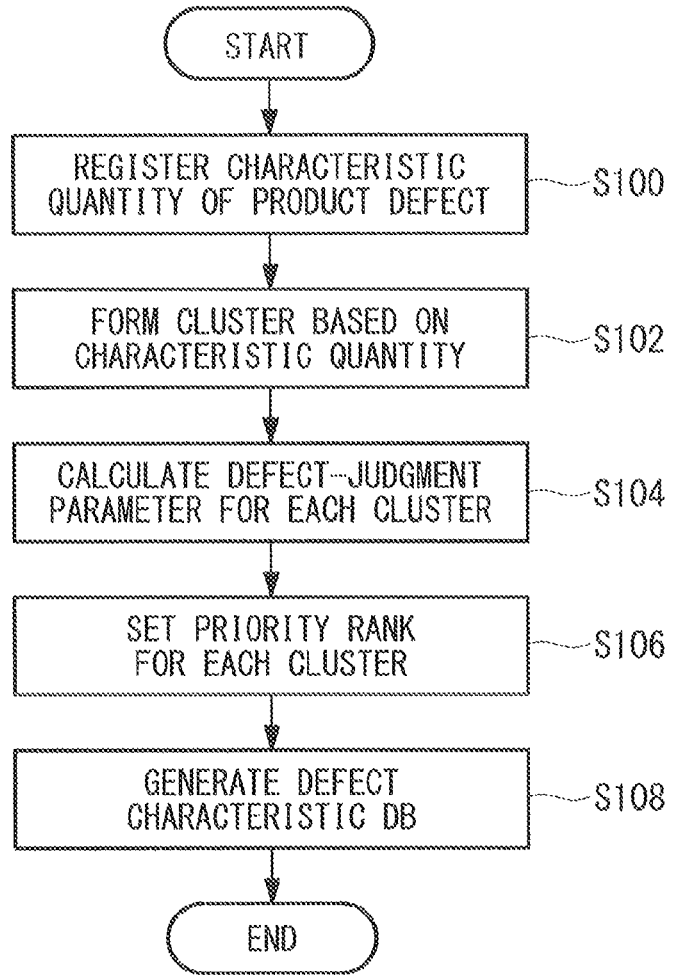
FIG. 3 is a flowchart showing the flow of defect-characteristic-database generating processing according to the first embodiment of the present invention.

FIG. 3 is a flowchart showing the flow of processing related to the generation of the defect characteristic DB (hereinafter referred to as "defect-characteristic-database generating processing"). The defect-characteristic-database generating processing is executed by the image processing device 20 or another information processing device (personal computer or the like).

First, in Step 100, a plurality of characteristic quantities of the product defects that have been judged to be defects by a person in advance (defect characteristic data) are registered (input to an information processing device) in association with the positions of those product defects (for example, the positions (x-y coordinates) with respect to the center of gravity of the product or the like).

Figure 4:
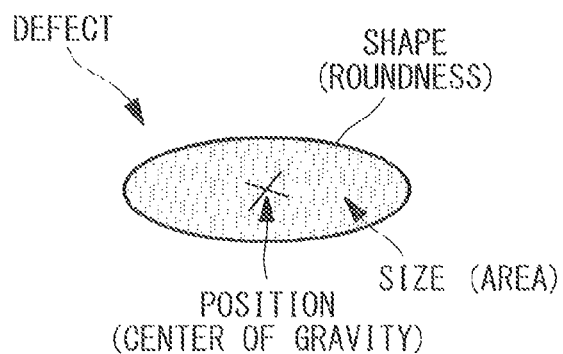
FIG. 4 is a schematic diagram showing characteristic quantities of a defect according to the first embodiment of the present invention.

The characteristic quantities of a product defect are defined by, for example, the size and shape thereof, as shown in FIG. 4.

The size of a product defect is the area of the product defect, and the area is determined based on, for example, the number of dots in an image assumed to be the product defect.

The shape of a product defect is assumed to be the roundness of the product defect. Assuming that the roundness is K, the area of the product defect is S, and the circumferential length of the product defect is L, the roundness is calculated by using Expression (1) below.

$$K = 4\pi \frac{S}{L^2} \quad \{\text{Eq. 1}\}$$

In Step 102 that follows, Euclidean distances among the plurality of registered product defects are calculated, and the product defects whose Euclidean distances are equal to or less than a predetermined threshold are assumed to be a single group (hereinafter referred to as "cluster").

Specifically, in Step 102, the Euclidean distances among the product defects are calculated, the product defects having the smallest Euclidean distances are assumed to be one cluster, Euclidean distances between the center of gravity (centroid) of this cluster and other product defects are calculated, and the closest product defects are also included in the same cluster. Then, Step 102 is repeated until the Euclidean distances between the cluster and the product defects exceed the threshold described above. By doing so, the product defects are classified based on the clusters.

In Step 104 that follows, defect-judgment parameters for the individual clusters determined in Step 102 are calculated. The defect-judgment parameters are parameters used to judge whether or not the defect candidates extracted from the detected-image data are defects, for example, the sizes and shapes of the product defects.

Specifically, in Step 104, an average size Sm, a standard deviation δS of the size, an average shape Kin, and a standard deviation δK of the shape are calculated for the product defects that constitute each cluster. By doing so, the size $Sm\pm\delta S$ and the shape $Km\pm\delta K$ for the product defects that constitute each cluster are obtained as defect-judgment parameters.

In Step 104, presence ranges for the individual clusters (for example, two-dimensional coordinates of two points) are defined.

In Step 106 that follows, priority ranks of the individual clusters are set.

In this Step, as an example, higher priority ranks are set for the clusters including a greater number of product defects.

In Step 108 that follows, a defect characteristic DB is generated by associating the individual clusters with the defect-judgment parameters calculated for the individual clusters in Step 104, the number of product defects included in the clusters, and the presence ranges of the clusters, which are the characteristic quantities of the clusters, and then, this processing is terminated.

Table 1 below shows an example configuration of the defect characteristic DB, and the cluster characteristic quantities are associated with each cluster Ci (i is an identifier of the cluster). Because the characteristic quantities of the product defects included in a cluster are associated with the individual product defects included in that cluster, the number thereof is the same as a number of defects Ni.

Hereinafter, the cluster characteristic quantities, the characteristic quantities of the product defects included in the cluster, and priority ranks shown in Table 1 are, as a whole, reterred to as attribute information of the cluster.

{Table 1}

Figure 5:
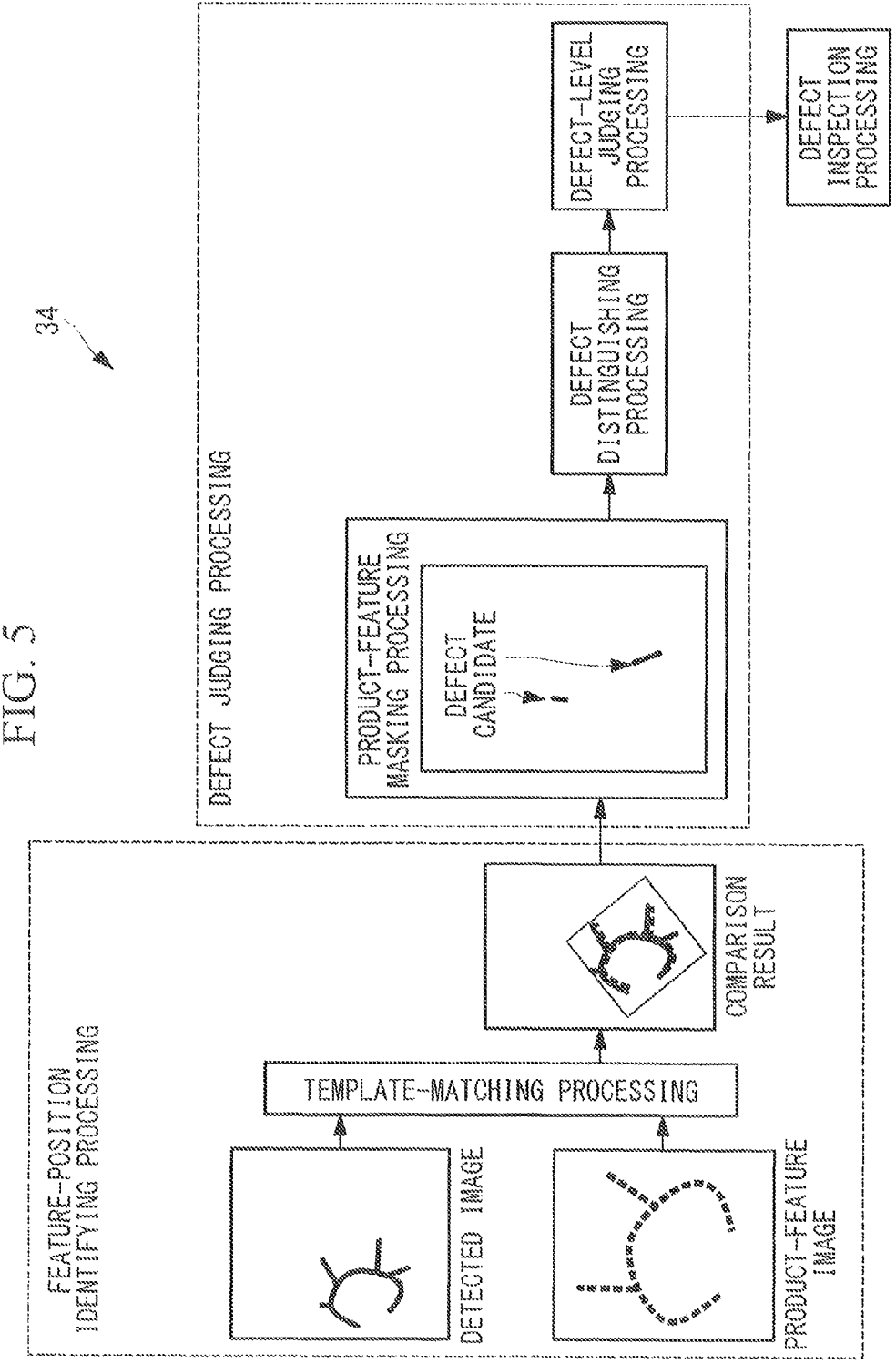
FIG. 5 is a schematic diagram showing the flow of processing performed by a product-defect judging portion according to the first embodiment of the present invention.

FIG. 5 is a schematic diagram showing the flow of processing performed by the product-defect judging portion 34 according to the first embodiment.

First, the feature-position identifying portion 38 performs the feature-position identifying processing.

With the feature-position identifying processing, as an example, template matching processing is applied to a detected image indicated by the detected-image data and a product-feature image indicated by product feature image data, and the position of the product feature in the detected-image data is identified.

Specifically, with feature-position identifying processing, the product-feature image is used as a template, the product-feature image is compared with the detected image by being moved, rotated, and enlarged/shrunk, thus identifying the position of the product feature in the detected-image data. Then, with the feature-position identifying processing, position-identifying information that indicates a product position, a rotational angle, and the size on the FPD 16 provided in the radiographic device 12 is obtained based on the comparison result of the template matching processing.

By doing so, the position of the product feature in the detected-image data is identified regardless of the orientation and size of the product at the time at which the radiaographic device 12 radiates the radiation.

Next, the defect judging portion 40 performs the defect judging processing. The defect judging processing includes product-feature masking processing, defect distinguishing processing, and defect-level judging processing.

With the product-feature masking processing, a portion corresponding to the product-feature image in the detected-image data is masked by using the position-identifying information obtained by the feature-position identifying processing and the product-feature image data. By doing so, "image" portions in the peripheries of the product feature are extracted from the masked detected-image data as defect candidates. Extraction referred to here corresponds to extracting information about the defect candidates, such as positions, sizes, or the like, from the detected-image data.

With the defect distinguishing processing, characteristic quantities are calculated for the defect candidates obtained by the product-feature masking processing, thus distinguishing them.

The characteristic quantities of a defect candidate are the same as those of a product defect, and are defined by, as an example, the size and shape thereof. Because the method of calculating the characteristic quantities of a defect candidate is the same as the method of calculating the characteristic quantities of a product defect used in the generation of the detect characteristic DB described above, a description thereof will be omitted.

With the defect-level judging processing, the presence/absence of a product defect is judged based on the characteristic quantities of the product defects indicated by the defect characteristic DB (the characteristic quantities of the cluster in this first embodiment) and the characteristic quantities of the defect candidates.

Figure 6:
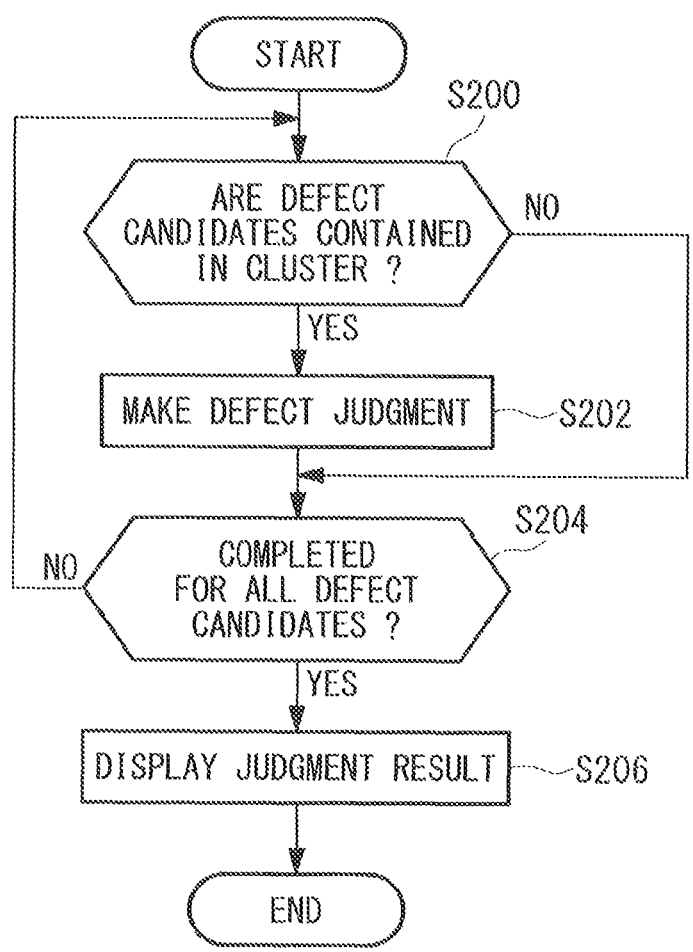
FIG. 6 is a flowchart showing the flow of defect-level judging processing according to the first embodiment of the present invention.

FIG. 6 is a flowchart showing the flow of the defect-level judging processing.

First, in Step 200, it is judged whether or not the defect candidates are contained in the clusters.

Specifically, it is judged whether or not the positions of the defect candidates extracted by the product-feature masking processing are contained in the presence ranges of any one of the clusters indicated by the defect characteristic DB.

If Step 200 results in an affirmative judgment, the process proceeds to Step 202, and if the result is a negative judgment, the process proceeds to Step 204.

In Step 202, it is judged whether or not the defect candidates that have been judged to be contained in the presence ranges of the clusters are product defects.

Specifically, it is judged whether or not the defect candidates are defects based on whether or not the sizes (defect sizes) and shapes (defect shapes) of the defect candidates satisfy the Judgment Expression below, which is based on the characteristic quantities (average defect size $Smi$, standard deviation $\delta Si$ of the defect size, average defect shape $Kmi$, and standard deviation $\delta Ki$ of the defect shape) of the clusters that are assumed to contain the defect candidates.

$$Smi-\alpha i \cdot \delta Si < \text{defect size} < Smi+\alpha i \cdot \delta Si$$

$$Kmi-\beta i \cdot \delta Ki < \text{defect shape} < Kmi+\beta i \cdot \delta Ki$$

In the above-described Judgment Expression, $\alpha i$ and $\beta i$ are parameters that are empirically obtained in advance for judging whether or not the defect candidates are product defects.

In Step 204 that follows, it is judged whether or not the processing in Steps 200 and 202 have been completed for all defect candidates; if the result is an affirmative judgment, the process proceeds to Step 206, and, if the result is a negative judgment, the process returns to Step 200.

In Step 206, results of the defect judgment in Step 202 and the defect candidates that have been judged not to be contained in the clusters in Step 200 are displayed on the display device 22.

In Step 206, the defect candidates contained in a cluster whose priority rank, which is included in the attribute information of the cluster, is higher are judged as being more likely to be defects. Then, the detected image based on the detected-image data obtained by the FPD 16 and the defect candidates that are displayed with emphasis are displayed on the screen of the display device 22, and the priority ranks are displayed for each of the defect candidates.

Upon completing Step 206, the defect-level judging processing is completed.

Figure 7:
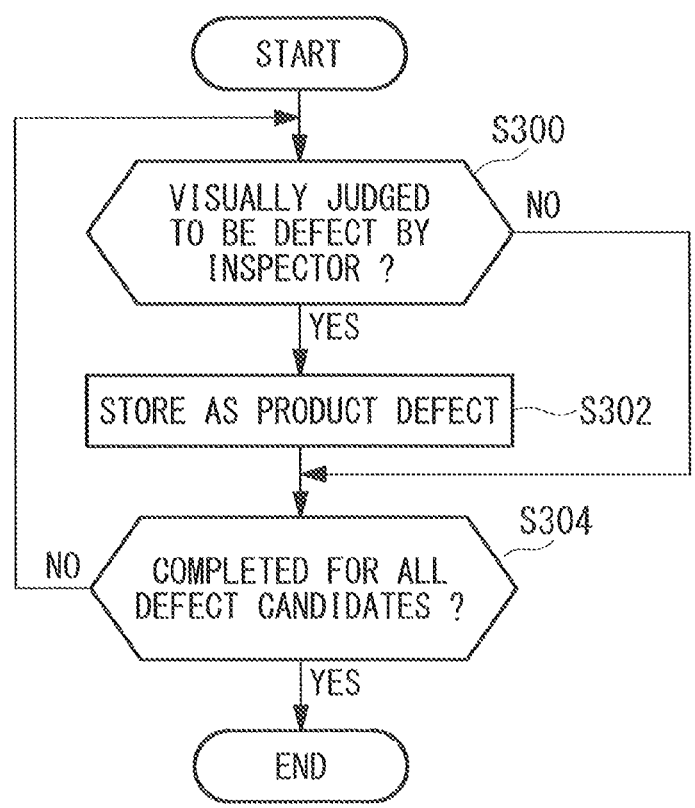
FIG. 7 is a flowchart showing the flow of defect inspection processing according to the first embodiment of the present invention.

Once the defect-level judging processing is completed, defect inspection processing shown in FIG. 7 is performed next. The defect inspection processing is processing for an inspector to visually make a final judgment about whether or not the defect candidates are defects based on the results of the defect judgment displayed on the display device 22 via the defect-level judging processing.

First, in Step 300, the inspector visually judges whether or not the defect candidates displayed on the display device 22 are defects. At this time, because the defect candidates are displayed on the display device 22 so that those that are likely to be defects are displayed with higher ranks, the inspector can easily judge whether or not the defect candidates are defects.

If the Step 300 results in an affirmative judgment, the process proceeds to Step 302, and, if the result is a negative judgment, the process proceeds to Step 304.

In Step 302, the characteristic quantities of the defect candidates that have been judged to be product defects are stored, as characteristic quantities of new product defects, in a temporary storage region of the storage device provided in the image processing device 20.

In Step 304, the inspector judges whether or not the visual defect judgment by the inspector has been completed for all defect candidates; if the result is an affirmative judgment, the defect inspection processing is terminated, and, if the result is a negative judgment, the process returns to Step 300.

Once the defect inspection processing is completed, the defect characteristic DB is subjected to updating processing for newly incorporating the defect candidates that have been judged to be product defects.

Specifically, the characteristic quantities of the new defect candidates stored in the temporary storage region in Step 302 of the defect inspection processing are incorporated to the characteristic quantities of the product defects included into the clusters that contain the new product defects. Then, in consideration of the characteristic quantities of the newly incorporated product defects, the characteristic quantities of the existing clusters are newly calculated, and the defect characteristic DB is updated.

By doing so, because the characteristic quantities of new product defects are accumulated in the defect characteristic DB every time the number of times that defect judgment is performed increases, the image processing device 20 can further increase the precision of the defect judgment.

As has been described above, with the image processing device 20 according to the first embodiment, the position of the product feature in the detected-image data is identified based on the shapes of the product feature indicated by the feature data stored in the DB storage portion 36 in advance, the defect candidates are extracted with reference to the identified product feature in the detected-image data, and the presence/absence of a product defect is judged based on the characteristic quantities (the characteristic quantities of the clusters in this first embodiment) of the product defects indicated by the defect characteristic DB, which is stored in the DB storage portion 36 in advance, and the characteristic quantities of the defect candidates.

Therefore, with the image processing device 20, it is possible to judge a product defect with high precision without performing work to fix relative positions of the product and the radiographic device 12 to predetermined positions.

Second Embodiment

A second embodiment of the present invention will be described below.

Because the configuration of the radiography system 10 according to the second embodiment is the same as the configuration of the radiography system 10 according to the first embodiment shown in FIGS. 1 and 2, a description thereof will be omitted.

In the first embodiment, the priority ranks of the clusters in the defect characteristic DB are determined based on the number of product defects included in the clusters; in the second embodiment, however, higher ranks are given to clusters included in a region that is known, a priori, to be prone to having product defects or clusters that are adjacent to that region.

Specifically, the contents of the defect characteristic DB can be changed manually by someone, and the inspector can change the priority ranks of the clusters.

By doing so, the radiography system 10 can further increase the precision of the defect judgment.

Third Embodiment

A third embodiment of the present invention will be described below.

Because the configuration of the radiography system 10 according to the third embodiment is the same as the configuration of the radiography system 10 according to the first embodiment shown in FIGS. 1 and 2, a description thereof will be omitted.

In the first embodiment, the characteristic quantities of the product defects included in the cluster containing the defect candidates are incorporated, and the characteristic quantities of the existing clusters are newly calculated; in the third embodiment, however, the characteristic quantities of the existing clusters are deleted after incorporating into the defect characteristic DB the characteristic quantities of the product defects stored in the temporary storage region in Step 302 of the defect inspection processing, and clusters are recalculated based on the characteristic quantities of all product defects accounting for the characteristic quantities of the newly incorporated product defects.

By doing so, even if appropriate clusters are not formed in an initial state in which little information is available about the product defects, because the information about the product defects is increasingly accumulated by repeating the defect judgment, thus calculating more appropriate clusters, a defect characteristic DB with which the precision of the defect judgment can be further increased is generated.

Fourth Embodiment

A fourth embodiment of the present invention will be described below.

Because the configuration of the radiography system 10 according to the fourth embodiment is the same as the configuration of the radiography system 10 according to the first embodiment shown in FIGS. 1 and 2, a description thereof will be omitted.

The configuration of the defect characteristic DB according to the fourth embodiment differs from that of the first embodiment.

With the defect characteristic DB according to the fourth embodiment, the product defects are classified in accordance with a plurality of regions (hereinafter referred to as "judgment regions") determined with reference to the position of the product feature, thus showing the characteristic quantities of the product defects for the individual judgment regions. The judgment regions are, for example, as shown in FIG. 8, individual quadrants that divide the detected-image data into four quadrants whose center ((x,y)=(0,0)) is at the center of gravity of the product feature.

Table 2 below shows an example configuration of the defect characteristic DB according to the fourth embodiment, and the judgment-region characteristic quantities are associated with individual judgment regions An. Because the characteristic quantities of the product defects included in a judgment region are associated with the individual product defects included in that judgment region, the number thereof is the same as the number of defects Ni.
{Table 2}

Then, with the defect-level judging processing according to the fourth embodiment, the quadrants in which the defect candidates are contained and the judgment regions that indicate those quadrants are judged.

Because the radiography system 10 according to the fourth embodiment identifies the positions of the defect candidates with reference to the position of the product feature, it becomes clear in which quadrant the defect candidates are positioned, and therefore, it is possible to judge the presence/absence of a product defect in a simpler manner with high precision based on the characteristic quantities of the judgment regions corresponding to the identified quadrants and the characteristic quantities of the defect candidates.

As above, although the present invention has been described by using the individual embodiments described above, the technical scope of the present invention is not limited to the scope of the embodiments described above. Within a range that does not depart from the scope of the invention, it is possible to incorporate various alterations and improvements to the individual embodiments described above, and the technical scope of the present invention also encompasses forms in which such alterations or improvements are incorporated.

For example, in the individual embodiments described above, although forms in which the image-acquisition device that obtains the detected-image data (digital data) by detecting the X-rays that have passed through the inspection subject is assumed to be the FPD 16 have been described, the present invention is not limited thereto, and it is permissible to employ a form in which an image of the X-rays that have passed through the inspection subject is captured on a silver film or an IP (imaging plate) to obtain an analog image, and the analog image is converted to digital data.

In addition, in the individual embodiments described above, although forms in which the radiation to be made to pass through the inspection subject is assumed to be X-rays have been described, the present invention is not limited thereto, and it is permissible to employ a form in which another type of radiation, such as γ-rays, electron beams (β-rays), or the like, is used as the radiation to be made to pass through the inspection subject.

In addition, in the individual embodiments described above, although forms in which the shape of a product defect is determined based on the roundness have been described, the present invention is not limited thereto, and it is permissible to employ a form in which the shape of a product defect is assumed to be a line having a directionality (diagonal, vertical, horizontal, or the like) with respect to a point or a product feature.

In addition, in the individual embodiments described above, although forms in which the detected-image data are assumed to be two-dimensional image data have been described, the present invention is not limited thereto, and it is permissible to employ a form in which three-dimensional image data obtained by irradiating the product with radiation from multiple angles are used.

In the case of this form, in the above-described fourth embodiment, instead of four quadrants, the detected-image data may be divided into eight quadrants that include the Z-direction.

In addition, the flows of the feature-position identifying processing and the defect judging processing described in the individual embodiments described above are also examples, and, within a range that does not depart from the scope of the present invention, it is permissible to eliminate unnecessary processing, to add new processing, or to switch the order of processing.

REFERENCE SIGNS LIST 10 radiography system
12 radiographic device
20 image processing device
34 product-defect judging portion
36 DB storage portion
38 feature-position identifying portion
40 defect judging portion

TABLE 1

| | CLUSTER: Ci |
|---|---|
| CLUSTER CHARACTERISTIC QUANTITY | NUMBER OF PRODUCT DEFECTS INCLUDED IN CLUSTER Ci:Ni<br>PRESENCE RANGE: FROM (xsi, yxi) TO (xei, yei)<br>AVERAGE DEFECT SIZE: Smi<br>STANDARD DEVIATION OF DEFECT SIZE: δSi<br>AVERAGE DEFECT SHAPE: Kmi<br>STANDARD DEVIATION OF DEFECT SHAPE: δKi |
| CHARACTERISTIC QUANTITY OF PRODUCT DEFECT INCLUDED IN CLUSTER | PRODUCT-DEFECT POSITION: (xij, yij)<br>DEFECT SIZE: Sij<br>DEFECT SHAPE: Kij |
| PRIORITY RANK: X | |

TABLE 2

| | JUDGMENT REGION: An |
|---|---|
| JUDGMENT-REGION CHARACTERISTIC QUANTITY | NUMBER OF PRODUCT DEFECTS INCLUDED IN JUDGMENT REGION An: Ni<br>PRESENCE RANGE: $N^{TH}$ QUADRANT (N IS ANY OF 1 TO 4)<br>AVERAGE DEFECT SIZE: Smi<br>STANDARD DEVIATION OF DEFECT SIZE: δSi |

TABLE 2-continued

| | JUDGMENT REGION: An |
|---|---|
| | AVERAGE DEFECT SHAPE: Kmi |
| | STANDARD DEVIATION OF DEFECT SHAPE: δKi |
| CHARACTERISTIC QUANTITY | PRODUCT-DEFECT POSITION: (xij, yij) |
| OF PRODUCT DEFECT INCLUDED | DEFECT SIZE: Sij |
| IN JUDGMENT REGION | DEFECT SHAP: Kij |

PRIORITY RANK: X

The invention claimed is:

1. A defect judging device that judges a presence/absence of a defect in an inspection subject based on detected-image data obtained by a radiographic device provided with a radiation source that irradiates the inspection subject with radiation and an imaging device that obtains the detected-image data by detecting the radiation that has passed through the inspection subject, the defect judging device comprising:
    a position identifying portion for identifying a position of a feature site in the detected-image data based on a shape of the feature site of the inspection subject indicated by feature data that are stored in the storage portion in advance; and
    a defect judging portion for extracting a defect candidate with reference to the feature site in the detected-image data identified by the position identifying portion and judging the presence/absence of a defect in the inspection subject based on a characteristic quantity of a defect indicated by defect characteristic data stored in the storage portion in advance and a characteristic quantity of the defect candidate,
    wherein the position identifying portion uses a product-feature image indicated by the feature data as a template, compares the product-feature image being moved, rotated, and enlarged/shrunk with a detected image indicated by the detected-image data so as to identify a position of a product feature in the detected-image data, and based on the comparison result, identifies the position of the feature site on the imaging device included in the radiographic device.

2. The defect judging device according to claim 1, wherein the defect judging portion masks the feature site in the detected-image data identified by the position identifying portion and extracts the defect candidate from the masked detected-image data.

3. The defect judging device according to claim 1, wherein the defect judging portion determines a position of the defect candidate with respect to the feature site and judges the presence/absence of a defect in the inspection subject based on the characteristic quantity of the defect indicated by the defect characteristic data in accordance with the position of the defect candidate and the characteristic quantity of the defect candidate.

4. The defect judging device according to claim 3, wherein defects whose Euclidean distances are equal to or less than a predetermined threshold are assumed to be a single group, and the defect characteristic data indicate characteristic quantities of individual groups.

5. The defect judging device according to claim 4, wherein respective priority ranks are set for the individual groups, and
    wherein the defect judging portion judges that the defect candidate contained in a presence range of one of the individual groups having a higher priority rank is more likely to be a defect.

6. The defect judging device according to claim 3, wherein, in the defect characteristic data, defects are classified in accordance with a plurality of regions determined with reference to the position of the feature site, thus showing the characteristic quantity of the defect for individual regions.

7. The defect judging device according to claim 1, wherein the defect characteristic data is updated by newly incorporating the characteristic quantity of the defect candidate that has been judged to be a defect.

8. A radiography system comprising:
    a radiographic device that radiates radiation onto an inspection subject and obtains detected-image data by detecting radiation that has passed through the inspection subject; and
    a defect judging device according to claim 1.

9. A defect judging method for judging a presence/absence of a defect in an inspection subject based on detected-image data obtained by a radiographic device provided with a radiation source that irradiates the inspection subject with radiation and an imaging device that obtains the detected-image data by detecting the radiation that has passed through the inspection subject, the defect judging method comprising:
    identifying a position of a feature site in the detected-image data based on a shape of the feature site of the inspection subject indicated by feature data that are stored in advance; and
    extracting a defect candidate with reference to the feature site in the detected-image data and judging the presence/absence of a defect in the inspection subject based on a characteristic quantity of a defect indicated by defect characteristic data stored in advance and a characteristic quantity of the defect candidate,
    wherein the identifying the position of the feature site comprises using a product-feature image indicated by the feature data as a template, comparing the product-feature image being moved, rotated, and enlarged/shrunk with a detected image indicated by the detected-image data so as to identify a position of a product feature in the detected-image data, and based on the comparison result, identifying the position of the feature site on the imaging device included in the radiographic device.

* * * * *